United States Patent
Gratwohl et al.

(10) Patent No.: US 7,789,863 B2
(45) Date of Patent: Sep. 7, 2010

(54) NEEDLE PROTECTING DEVICE COMPRISING A RELEASEABLY BLOCKED NEEDLE PROTECTOR

(75) Inventors: Christian Gratwohl, Aarau (CH); Martin Wymann, Liebefeld (CH); Marc Lanz, Lobsigen (CH); Urs Widmer, Bern (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/850,119

(22) Filed: Sep. 5, 2007

(65) Prior Publication Data

US 2008/0103454 A1 May 1, 2008

(30) Foreign Application Priority Data

Sep. 6, 2006 (DE) ......... 10 2006 041 808

(51) Int. Cl.
*A61M 5/32* (2006.01)
(52) U.S. Cl. ..................................... 604/192
(58) Field of Classification Search ......... 604/192–198, 604/110; 401/99, 109–114, 243
See application file for complete search history.

(56) References Cited

U.S. PATENT DOCUMENTS 4,911,693 A * 3/1990 Paris ..................... 604/192
5,195,983 A * 3/1993 Boese ..................... 604/192
5,882,342 A * 3/1999 Cooper et al. ............. 604/195

FOREIGN PATENT DOCUMENTS

| DE | 10009816 A1 | 10/2001 |
| DE | 10044383 A1 | 4/2002 |
| DE | 10203597 A1 | 8/2003 |
| DE | 202004016791 U1 | 12/2004 |

* cited by examiner

*Primary Examiner*—Kevin C Sirmons
*Assistant Examiner*—Bradley J Osinski
(74) *Attorney, Agent, or Firm*—Dorsey & Whitney LLP; David E. Bruhn. Esq.

(57) ABSTRACT

A needle protecting device on or for an injection apparatus comprising an injection needle with a needle tip and a needle base beyond which the injection needle protrudes, the needle protecting device including a needle protector moveable from an exposing position in which the needle tip is exposed to a protective position in which it overlaps the needle tip, a first blocking mechanism connected to or formed in one piece with one of the needle protector or the needle base, and a second blocking mechanism connected to or formed in one piece with the other of the needle protector or the needle base, wherein, when the needle protector is in the protective position, the blocking mechanisms are engaged with each other preventing the needle protector from moving into the exposing position, and wherein the engagement may be non-destructively released and/or restored.

19 Claims, 3 Drawing Sheets

NEEDLE PROTECTING DEVICE COMPRISING A RELEASEABLY BLOCKED NEEDLE PROTECTOR

CROSS-REFERENCE TO RELATED APPLICATIONS

This application claims benefit of priority to German Application No. DE 10 2006 041 808.5 filed on Sep. 6, 2006, the content of which is incorporated in its entirety herein by reference.

BACKGROUND

The present invention relates to devices for injecting, infusing, administering, delivering and dispensing substances, and to methods for making and using such devices, as well as to related peripheral, adjunct, complementary, cooperative and auxiliary devices and methods. More particularly, the present invention relates to a needle protecting device on or for devices for injecting, infusing, administering, delivering and dispensing substances.

A needle protecting device can be a fixed part of an injection device, but is typically provided for attachment to an injection device, or is detachably attached thereto. Needle protecting devices are used in the administration of substances or products, e.g. medicines, for example insulin, and can be used in self-administering, i.e. by patients who administer the relevant product themselves. The injection apparatus or devices involved can take the form of a simple syringe, including syringes which are disposed of after a single use. However, injection apparatus may be reusable, and may allow the dosage or amount of the product or substance to be administered to be set or selected. Such injection apparatus can take the form of injection pens, such as re used in diabetes therapy and, more recently, also in other therapies.

When handling injection apparatus, there is the danger of patients or medical staff injuring or sticking themselves on the point or tip of a needle, and/or infecting themselves via a stick from a used injection needle. Needle protecting devices comprising a movable needle protector have been developed to prevent this. Typically a needle protector can be moved back and forth in the longitudinal direction or along the length of the injection needle and, once used, may be automatically blocked or locked in a distal or forward protective position, such that it can no longer be moved in the proximal or rearward direction and the injection needle or at least its tip can no longer be exposed. Such needle protecting devices are for example known from WO 01/91837 A1 and U.S. Pat. No. 6,773,415 B2.

Needle protecting devices which are intended for a single use have to be mass-produced at low cost. On the other hand, they should function properly to prevent injuries and infection.

SUMMARY

It is an object of the present invention to provide a needle protector or needle protecting device that provides an optimal amount of protection and operates properly and conveniently.

In one embodiment, a needle protecting device in accordance with the present invention comprises a releaseably lockable movable needle protector.

A needle protecting device for an injection apparatus comprising an injection needle with a needle tip and a needle base beyond which the injection needle protrudes, the needle protecting device comprising a needle protector moveable from an exposing position exposing the needle tip to a protective position overlapping the needle tip, a first lock element associated with one of the needle protector or the needle base, and a second lock element associated with the other of the needle protector or the needle base, wherein, when the needle protector is in the protective position, the lock elements are in engagement preventing the needle protector from moving into the exposing position, and wherein the engagement may be non-destructively released and restored.

In one embodiment, the present invention comprises a needle protecting device for an injection apparatus comprising an injection needle with a needle tip and a needle base beyond which the injection needle protrudes, the needle protecting device comprising a needle protector moveable from an exposing position in which the needle tip is exposed to a protective position in which the protector overlaps the needle tip, a first blocking mechanism associated with one of the needle protector or the needle base, and a second blocking mechanism associated with the other of the needle protector or the needle base, wherein, when the needle protector is in the protective position, the blocking mechanisms are engaged with each other preventing the needle protector from moving into the exposing position, and wherein the engagement may be non-destructively released and/or restored.

In one embodiment of the present invention, the invention comprises a method for functionally testing a needle protecting device for an injection apparatus comprising an injection needle with a needle tip and a needle base beyond which the injection needle protrudes, the needle protecting device comprising a needle protector moveable from an exposing position in which the needle tip is exposed to a protective position in which the protector overlaps the needle tip, a first lock element associated with one of the needle protector or the needle base, and a second lock element associated with the other of the needle protector or the needle base, wherein, when the needle protector is in the protective position, the lock elements are engaged with each other preventing the needle protector from moving into the exposing position, and wherein the engagement of the lock elements may be non-destructively released and restored, the method comprising the steps of: when the needle protector is in the protective position, moving the first lock element out of the engagement using a tool, applying an external force to the needle protector thereby moving the protector in a proximal direction, and removing the external force whereby the needle protector, if functioning properly, moves into the protective position again.

In one embodiment, the present invention comprises a needle protecting device on or for an injection apparatus, which comprises an injection needle comprising a needle tip and a needle base. The needle base serves to mount the injection needle, and can be formed in a conventional way as a needle holder, into which the injection needle protrudes and which holds the injection needle fixedly, e.g. in a material lock. The injection needle protrudes beyond the needle base in a longitudinal direction, i.e., along the longitudinal length of the injection apparatus. The needle protecting device is movably connected to the needle base, and comprises a block or lock for blocking the device in a protective position.

In some embodiments, the injection needle can protrude through the needle base. In principle, however, the needle base and the injection needle can be formed in one piece. The needle protector can be moved in the distal or forward direction relative to the needle base and the injection needle, from an exposing position in which the needle tip of the injection needle protrudes beyond the needle protector into a protective position in which it overlaps the injection needle including the needle tip.

In some preferred embodiments, the needle protector is sleeve-shaped, such that it surrounds the injection needle, including the needle tip, in the protective position. In some embodiments, the needle protector forms an opaque covering around the injection needle, but can also be transparent, for example consisting of a transparent material or comprising through-holes. In principle, one or more fingers extending alongside the needle in the longitudinal direction would also be sufficient as the needle protector. The needle protector serves to protect against injury from an injection portion of the injection needle. In such embodiments, the needle protector moves in the distal or forward direction from the exposing position into the protective position.

In some embodiments, the needle protector of the present invention comprises a block or lock that comprises a first blocking or lock mechanism and a second blocking or lock mechanism. The first blocking mechanism is formed on one of the needle protector and the needle base or formed separately and connected to the relevant component. The first blocking mechanism is movably formed on or movably connected to one of the needle protector and the needle base such that it can be moved together with the one of the needle protector and the needle base, relative to the other of the needle protector and the base, and/or can also be moved relative to said one of the needle protector and the needle base. The second blocking mechanism formed on the other of the needle protector and the needle base or, if formed separately, is connected to the relevant other component. When the needle protector is in the protective position, the first blocking mechanism and second blocking mechanism are in engagement with each other, preventing the needle protector from moving in the proximal (i.e., rearward) direction. In some embodiments, the second blocking mechanism is stationary relative to the other of the needle protector and the needle base. It at least cannot be moved relative to the other of the needle protector and the needle base in the longitudinally with respect to the injection needle when the needle protector is in the protective position, thus being able to fulfil the locking function.

In accordance with some embodiments of the present invention, the blocking or lock engagement can be non-destructively released. In some embodiments, a tool is used to release it. When in blocking engagement, the blocking mechanisms prevent the needle protector from being moved into the exposing position unintentionally or by a force exerted on the needle protector from without. The protective function is thus facilitated. In some embodiments, the blocking engagement can be released by a type of manipulation which is not immediately obvious to the user. For example, at least two manipulations may be required in a certain order, one after the other. In some embodiments, the manipulation or at least one of the number of manipulations may be performed only by a tool.

In some preferred embodiments, the needle protecting device includes a spring member which charges or urges the needle protector with a spring force acting in the distal or forward direction. The spring force causes the needle protector to automatically move into the protective position after administering the product if a force overcoming the spring force is not exerted on it. The spring member is supported in the direction of the spring force on the needle protector and in the opposite direction on the needle base, either on both or on one of these components, directly or as applicable also only via one or more intermediate members. The spring member can, for example, be a pneumatic or mechanical spring or force generator. In terms of its function, it can be a pressure spring. With respect to its shape, a spiral spring may be preferred.

Before being used, the needle protector advantageously assumes an initial position in which it overlaps the injection needle including the needle tip. The needle protector is not, however, blocked or locked in the initial position, but rather can be moved into an exposing position, against the restoring force of the spring member, wherein it is entirely conceivable and also advantageous not only for the needle protector to be held in the initial position due to the spring force but also additionally for there to also be a frictional lock or advantageously a positive lock which requires a certain force to be applied in the proximal or rearward direction to overcome it. The frictional or positive lock may be released when the needle protector is charged in the proximal direction with a force such as usually occurs when the injection needle is injected into human skin. By contrast, the blocking engagement in the protective position can only be released by a force exerted on the needle protector from without by destroying at least one of the blocking mechanisms involved in the blocking engagement. In the initial position, the needle protector charged with the spring force does provide a certain but limited protective function, but can additionally serve as a blind, to remove self-administering users' fear of injecting. From the point of view of its protective function, however, it would also be possible for the needle protector to assume the exposing position before use.

In some embodiments, to enable the blocking engagement to be non-destructively released, the first blocking mechanism can be movably connected to said one of the needle protector and the needle holder, in some preferred embodiments the needle protector. The connection is such that the first blocking mechanism can move relative to the needle protector and also relative to the needle base. If the first blocking mechanism is connected to the needle protector, the connection is also designed such that the needle protector slaves the first blocking mechanism when it moves in the longitudinally with respect to the length of the injection needle.

In some embodiments, it is advantageous if a restoring spring force acts on the first blocking mechanism to counteract the movements of the first blocking mechanism relative to said one of the needle protector and the needle base. In this way, the first blocking mechanism is held in a position of equilibrium relative to said one of the needle protector and the needle base or, in the event of a deviation, is returned to the position of equilibrium. The spring member mentioned with respect to the needle protector can serve to generate the spring force for achieving equilibrium. In principle, however, a spring member can be provided for the first blocking mechanism only, either as a single spring member or in addition to the spring member which charges the needle protector with a spring force. If the same spring member acts on the first blocking mechanism and moves the needle protector into the protective position, such a spring member can act directly on the first blocking mechanism and charge the needle protector with the spring force via the first blocking mechanism.

In some embodiments, instead of forming the first blocking mechanism separately from said one of the needle protector and the needle base and movably connecting it to the relevant component in a joint or by a number of joints, a movable first blocking mechanism may be formed in one piece with the relevant component, wherein its ability to move is enabled by shaping it appropriately. In another alternative, the first blocking mechanism and the relevant component are formed separately from each other and connected to each other in a material lock. When the first blocking mechanism is formed in one piece or fixedly connected in a material lock, a restoring spring force which acts on the first blocking mechanism is based on dimensional elasticity. The first blocking mechanism can thus, for example, be elastically pliable. In some preferred embodiments, a first blocking mechanism is formed separately and connected in a joint to said one of the needle protector and the needle base. Such a first blocking mechanism can advantageously be rigid, i.e. inflexible, in its own right.

In some preferred embodiments, a needle protecting device in accordance with the present invention features a blocking portion which surrounds the needle protector or is surrounded by the needle protector. At least when in blocking engagement, the blocking mechanisms are within the axial length of the blocking portion. One of the needle protector and the blocking portion surrounds the blocking mechanisms in blocking engagement, at least when the needle protector is in the protective position, and in this way protect them from being accessed laterally. Neither of the blocking mechanisms in blocking engagement is visible from the side, such that the method of operation of the blocking is at least not immediately obvious to the user. Since the spatial arrangement is very tight and the injection needle is arranged centrally, the user cannot easily act on the blocking mechanisms in the longitudinally relative to the injection needle using a finger to release their blocking engagement. Rather, a specific tool is required to release the engagement, which in some preferred embodiments can be a straight or, as applicable, a bent rod. To release the blocking engagement or lock, the tool is moved through a distal or forward opening in the needle protector or the blocking portion and, at least substantially in the longitudinal direction of the injection needle, into the region of the blocking portion, and brought to bear on one of the blocking mechanisms. The blocking engagement can be released by pressing the tool at least substantially in the longitudinal direction of the injection needle against one of the blocking mechanisms, e.g., the first blocking mechanism. Other manipulations on the blocking mechanisms in blocking engagement are not required. The blocking mechanisms are formed accordingly and can be moved relative to each other in blocking engagement. Enabling them to be released by the action of pressure in the longitudinal direction facilitates automatic functional testing, such that this can advantageously be performed in a short period of time and with low demands on precision in positioning the needle protecting device to be tested or in controlling the movement which the tool or needle protector has to perform relative to the respective other component.

In some preferred embodiments, the first blocking mechanism is connected to said one of the needle protector and the needle base such that it can be tilted or pivoted. In accordance with some preferred embodiments, the first blocking mechanism may only exhibit the degree of freedom of an ability to tilt or pivot about one tilting or pivoting axis relative to said one of the needle protector and the needle base, wherein the relevant axis is stationary relative to said one of the needle protector and the needle base. As applicable, the first blocking mechanism can also be able to tilt or pivot about a number of axes relative to said one of the needle protector and the needle base. The axis or, as applicable, number of axes is/are advantageously not parallel to the injection needle, but rather extend/s transverse to the injection needle. In some preferred embodiments, the axis or number of axes is/are perpendicular to the injection needle and extend radially with respect to the injection needle. The injection needle is at least substantially straight, and at least sufficiently straight that it can be injected into and through human skin by a pressure force.

In a further development of the present invention, a needle protecting device in accordance with the present invention includes a third blocking mechanism which is formed together with the second blocking mechanism on the other of the needle protector and the needle base, or is connected to the relevant component. In this respect, the statements made regarding the second blocking mechanism also apply similarly to the third blocking mechanism. In a top view onto the cited tilting or pivoting axis, the second blocking mechanism and the third blocking mechanism are arranged on different sides of said axis, i.e. one to the left and the other to the right of the axis. The second blocking mechanism and third blocking mechanism each form a stopper for the first blocking mechanism. These stoppers are offset with respect to each other longitudinally relative to the length of the injection needle. When the needle protector is in the protective position, the first blocking mechanism is in pressing contact with at least one of the other two blocking mechanisms. If a force acting in the direction of the exposing position is exerted on the needle protector, the first blocking mechanism tilts or pivots in accordance with the axial offset which the other two blocking mechanisms exhibit with respect to each other, in pressing contact with the other of said two blocking mechanisms, such that the first blocking mechanism then abuts against both other blocking mechanisms.

In other developments of the present invention, an unblocking mechanism may be provided which forms another stopper for the first blocking mechanism. This stopper faces away from the stopper formed by the second blocking mechanism. In some preferred embodiments, the needle protecting device thus includes three stoppers, two of which point in the same direction, while the third points in the opposite direction. The stoppers can point in the proximal (rear) or distal (front) direction, i.e. with respect to a direction along the length of the injection needle or an injection device to which the needle is attached. If the first blocking mechanism is formed on or connected to the needle protector, such that it is slaved by its axial movements, the stoppers formed by the second blocking mechanism and third blocking mechanism point or extend in the distal direction, and the stopper formed by the unblocking mechanism accordingly points in the proximal direction. If the first blocking mechanism can be tilted about a tilting axis pointing transverse to the longitudinal direction of the injection needle, it is advantageous for the second blocking mechanism to have a smaller distance, as measured longitudinally, from the stopper of the third blocking mechanism than from the stopper of the unblocking mechanism. By arranging the stoppers in this way, the first blocking mechanism can perform tilting movements of different amplitudes, depending on the movement direction of the needle protector.

In some preferred embodiments, the second blocking mechanism is formed by a protrusion which projects transversely relative to the longitudinal axis of the needle, from a surface area of the needle protecting device, for example from the needle protector or from the above-mentioned blocking portion. The third blocking mechanism may be formed by another protrusion which projects from the surface area, likewise transversely relative to the needle. If the needle protecting device also features the unblocking mechanism, the latter may be formed by a protrusion which projects from the same surface area or, as applicable, from another surface area generally across the axis of the injection needle.

The present invention enables the proper functioning of the needle protecting device to be verified or tested at the end of the production process, thus encompassing a method of such testing. An advantage of the testing method of the present invention is that the needle protecting devices can be used properly after having been verified or tested, since the blocking engagement can be non-destructively released and/or restored. Accordingly, a method for testing the proper method of operation of the needle protecting device is also a subject of the present invention In one embodiment, for testing, the first blocking mechanism is moved out of the blocking engagement by a tool when the needle protector is in the protective position, and the needle protector is moved in the proximal (rear) direction by an external force, such that the needle tip protrudes beyond the needle protector. The needle protector is moved into the exposing position. The needle protector is then relieved of the external force and moves back in the distal (forward) direction. In the course of the movement in the distal direction, the blocking mechanisms pass back into blocking engagement, if functioning properly. It is possible to test that the blocking engagement has been restored by again applying an external force while omitting the manipulation performed using the tool. The testing method advantageously also includes this testing step.

If the needle protector assumes a non-blocked, distal initial position before the needle protecting device is used, some preferred embodiments of the testing method in accordance with the present invention include other steps preceding the steps mentioned above. In a first step of the testing method in such a further development, the needle protector is moved by an external force out of the distal, forward initial position, into the exposing position or at least in the direction of the exposing position and is relieved of the external force in the exposing position or, as applicable, earlier, such that it moves into the protective position. In a following step, the blocking engagement which is automatically set by this is released using the tool, as described.

When needle protecting devices in accordance with the present invention are serially produced, they can advantageously each be subjected to the testing method directly following their assembly, i.e. they are tested in-line with their assembly. In such method embodiments, an additional holder for holding, in a defined way, the respective needle protecting device to be tested is not required, since an assembly holder could be used to hold the devices, in a defined way, for testing. If the devices are tested by a holder provided especially for this purpose, they can still simply be automatically passed from the assembly holder—if the devices are assembled automatically—to the testing holder. In principle, however, off-line testing is also possible, wherein the needle protecting devices are first assembled and only later—as applicable, after intermediate storage or transport—tested for proper functioning. Off-line testing, however, may require each needle protecting device which is to be tested to be picked up again by the testing device or a holder associated with the testing device. In some embodiments of the method, testing by hand may also be feasible both for in-line and off-line testing.

DETAILED DESCRIPTION

Figure 1:
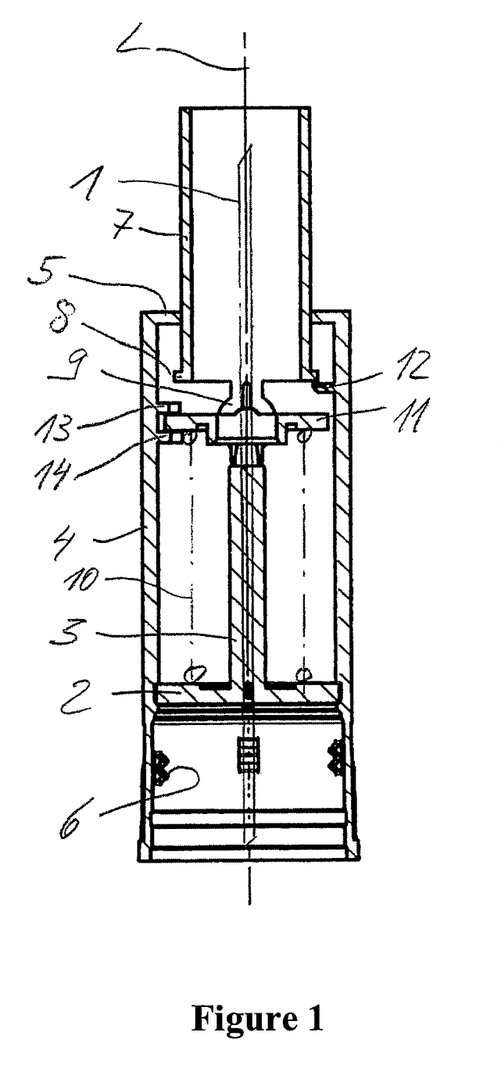
FIG. 1 depicts one embodiment of a needle protecting device in accordance with the present invention comprising a needle protector, in a distal, initial position.

FIG. 1 shows a needle protecting device in an initial position before an injection. The needle protecting device includes and/or is coupled to an injection needle 1 and a needle base which serves to position and attach the injection needle 1. The needle base comprises a flat bottom 2 and a central holding region 3 projecting from the bottom 2 in a distal direction. The injection needle 1 protrudes through the holding region 3, such that it protrudes beyond the needle base in the distal direction and in the proximal direction. The holding region 3 holds the injection needle 1 fixedly, such that it cannot move axially. The injection needle 1 is a cannula, i.e. a hollow needle.

The needle protecting device also includes a sleeve structure 4 which surrounds the needle base. The needle base is inserted into the sleeve structure 4 and connected to the sleeve structure 4 such that it cannot move in the longitudinal direction of the injection needle 1, relative to the sleeve structure 4. The needle base and the sleeve body 4 could, in principle, be formed from one piece. The sleeve structure 4 forms a attaching portion, proximal to the needle base 2, for attaching the needle protecting device to the distal end of an injection apparatus. The injection apparatus may be an injection pen such as is known from diabetes therapy and from other therapies, for example administering osteoporosis preparations or growth hormones. The needle protecting device can be detachably clipped onto the injection apparatus and, for this purpose, comprises a number of latching mechanisms 6, distributed in the circumferential direction, in its attaching portion. The attaching portion surrounds a connecting portion of the injection needle 1, which protrudes beyond the needle base in the proximal direction, at least up to a proximal needle tip. When attached onto the injection apparatus, the connecting portion of the injection needle 1 penetrates a sealing membrane which seals a distal end of a reservoir, for example a medicine ampoule. Once this membrane has been penetrated, the hollow volume of the injection needle 1 is fluidically connected to the reservoir.

The sleeve structure 4 surrounds the holding region 3 of the needle base distal to the bottom 2, and protrudes slightly beyond the holding region 3 in the distal direction.

Other parts of the needle protecting device are a needle protector 7 which can be moved along the injection needle 1 relative to the needle base and the sleeve structure 4, a spring member 10 which charges the needle protector 7 in the distal direction with a spring force, and a blocking means for blocking the needle protector 7 in a distal protective position. FIG. 1, however, shows the needle protecting device in an initial state in which the needle protector 7 assumes a distal initial position relative to the needle base and in particular the injection needle 1. The needle protector 7 can be moved out of the initial position in the proximal direction relative to the needle base, against the restoring spring force of the spring member 10. The needle protector 7 comprises a sleeve portion which surrounds the distal, forward needle portion of the injection needle 1 which protrudes distally beyond the needle base and the sleeve structure 4. The sleeve portion of the needle protector 7 protrudes through a distal opening in the sleeve structure 4. A flange 5 which protrudes inwards onto the injection needle 1 is formed on the distal end of the sleeve structure 4. The flange 5 guides the needle protector 7 axially and linearly and also forms an axial translational stopper up to which the needle protector 7 can be maximally moved in the distal direction due to the spring force of the spring member 10. In its initial position, however, the needle protector 7 does not axially abut against the flange 5 but is rather held in a different way, namely by a part of the locking structure.

The locking structure, lock or lock system (which also may be referred to as a blocking mechanism or blocking means) includes a first blocking mechanism 11 which is connected to the needle protector 7 such that it can be moved together with or also relative to the needle protector 7. The first blocking mechanism 11 exhibits one degree of freedom of movement relative to the needle protector 7, namely an ability to rotate about an axis K which is not parallel to the longitudinal axis L or injection needle 1. The axis K points radially with respect to the longitudinal axis L or injection needle 1 and forms a tilting axis for the first blocking mechanism 11 which is connected to the needle protector 7 such that it can tilt about the tilting axis K. The blocking mechanism also includes a second blocking mechanism 12 and a third blocking mechanism 13. The blocking mechanisms 12 and 13 are formed by protrusions which project inwards, i.e. in the direction of the central longitudinal axis L, from the sleeve body 4. The blocking mechanisms 12 and 13 are offset with respect to each other in the longitudinal direction of the injection needle 1 and are arranged on different sides of the tilting axis K. In the representation in FIG. 1, the second blocking mechanism 12 is arranged to the right of the tilting axis K and the third blocking mechanism 13 is arranged to the left of the tilting axis K. The second blocking mechanism 12 is also arranged distal to the third blocking mechanism 13.

In the initial state shown in FIG. 1, the blocking mechanisms 12 and 13 form axial stoppers for the first blocking mechanism 11 on their rear side respectively pointing in the proximal direction. The axial offset between these rear stoppers is selected such that the first blocking mechanism 11 cannot, within the scope of its ability to tilt, be moved out of the initial position in the distal direction, past the blocking mechanisms 12 and 13.

The lock system also includes an unblocking mechanism 14 which is likewise formed by a protrusion and projects inwardly from the sleeve structure 4. The unblocking mechanism 14 is arranged on the same side as the third blocking mechanism 13 with respect to the tilting axis K and is offset with respect to it in the proximal direction. Another protrusion on the side of the second blocking mechanism 12, proximal to it, is not formed. The unblocking mechanism 14 only protrudes inwards far enough that it does form a stopper for the first blocking mechanism 11 on its front side pointing in the distal direction, but the first blocking mechanism 11 cannot tilt out of the stopper contact and be moved past the unblocking mechanism 14 in the proximal direction when the needle protector 7 moves in the proximal direction. The first blocking mechanism 11 does protrude into a gap between the blocking mechanism 13 and the unblocking mechanism 14, however the blocking mechanism 13 likewise only projects from the sleeve body 4 far enough that the first blocking mechanism 11 can tilt out of the stopper contact with the unblocking mechanism 14.

Figure 2:
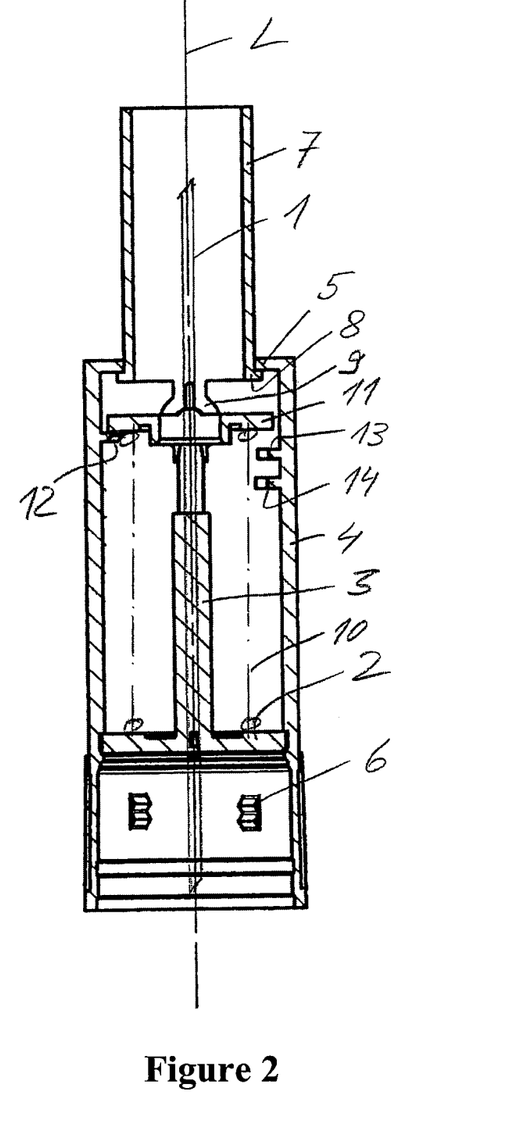
FIG. 2 depicts the needle protecting device of FIG. 1, with the needle protector in a distal, protective position.

FIG. 2 shows the needle protecting device in an end state, once used. In the end state, the needle protector 7 assumes a distal protective position in which the blocking mechanism locks it, such that it cannot be moved in the proximal (rearward) direction by an external force. The blocking mechanisms 12 and 13 each form a stopper for the first blocking mechanism 11, pointing in the distal direction, on their front side. The axial distance between these two stoppers is dimensioned such that when an attempt is made to move the needle protector 7 in the proximal direction, the first blocking mechanism 11 passes into stopper contact with the blocking mechanism 12 and, while maintaining this stopper contact, tilts into a stopper contact with the blocking mechanism 13. Due to the stopper contact on both sides, the first blocking mechanism 11 cannot pass the two blocking mechanisms 12 and 13 in the proximal direction, such that the needle protector 7 is blocked in the protective position. The two stoppers of the blocking mechanisms 12 and 13 which act when the needle protector 7 is in the protective position exhibit at least substantially the same distance from each other in the longitudinal direction L as the two stoppers formed on the rear sides of the blocking mechanisms 12 and 13, which prevent the needle protector 7 from being able to move from the initial position shown in FIG. 1 into the protective position. The blocking mechanisms 12 and 13, in co-operation with the first blocking mechanism 11, thus block the needle protector 7 in the proximal direction in the protective position and in the distal direction in the initial position.

Figure 3:
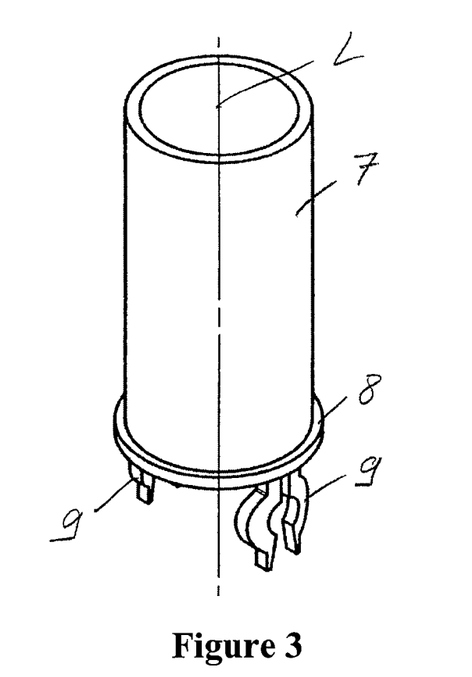
FIG. 3 depicts the needle protector in a perspective view.
Figure 4:
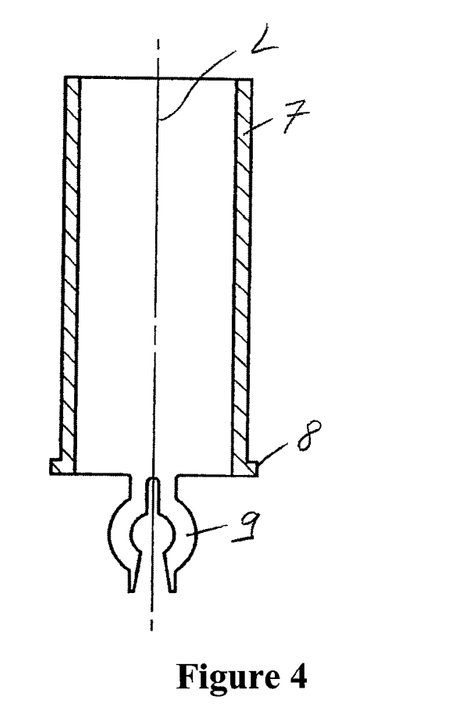
FIG. 4 depicts the needle protector in a longitudinal section.

FIGS. 3 and 4 show the needle protector 7 in a perspective view and in a longitudinal section. The needle protector 7 comprises the sleeve portion mentioned, which already surrounds the injection needle 1 when the needle protecting device is in its initial state and protrudes at least up to the height of the needle tip and, in some embodiments, beyond the needle tip in the distal direction. The sleeve portion is formed as an opaque, hollow-cylindrical covering. A flange 8 which projects radially outwards is formed on the proximal end and in the example embodiment encircles the longitudinal axis L, but could in principle also be formed by flange pieces spaced from each other in the circumferential direction, or as applicable a single flange piece only. The flange 8, together with the flange 5 of the sleeve structure 4, forms a pair of stoppers which co-operate to limit the movement by the needle protector 7 in the distal direction, i.e. which determine the most distal end position which the needle protector 7 can assume relative to the sleeve structure 4 and the needle base. The needle protector 7 also includes two attaching mechanisms 9 which project from the sleeve portion in the proximal direction. The attaching mechanisms 9 serve to connect the needle protector 7 to the first blocking mechanism 11 in a joint.

Figure 5:
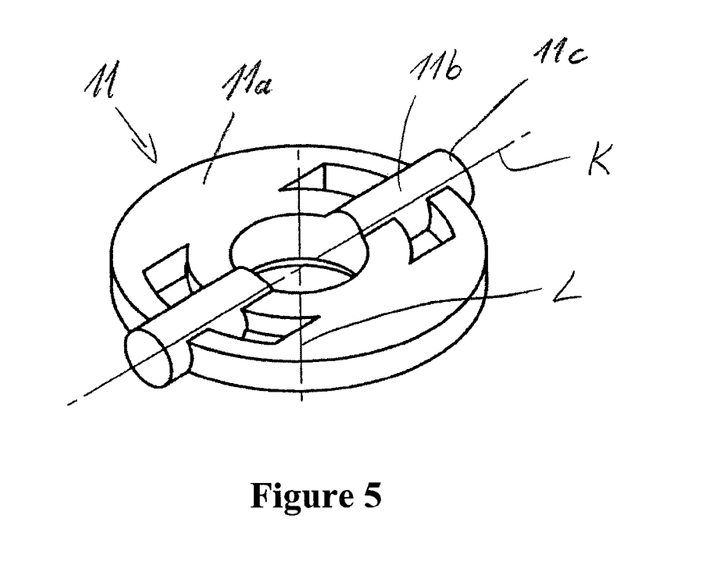
FIG. 5 depicts an embodiment of a first blocking mechanism of the needle protecting device, in a perspective view.

FIG. 5 shows the first blocking mechanism 11 in a perspective view. The blocking mechanism 11 comprises a disc-shaped base body 11a, two attaching mechanisms 11b and two rotational blocks 11c which are formed with the base body 11a in one piece. The rotational blocks 11c are each in guiding engagement with an assigned axial guide of the sleeve structure 4, said engagement preventing rotational movements of the first blocking mechanism 11 and thus rotational movements of the needle protector 7 about the longitudinal axis L. In this exemplary embodiment, the rotational blocks 11c protrude slightly beyond the base body 11a, transverse to the longitudinal direction L. The two assigned guides of the sleeve structure 4 are axial grooves, but could, for example, also be axial ribs which project inwardly on the inner surface area of the sleeve structure 4. In the case of projecting ribs, the rotational blocks 11c could also be replaced with recesses. A single rotational block is in principle sufficient. However, rotational blocks arranged offset with respect to each other in the circumferential direction about the longitudinal axis L, such as for example the rotational blocks 11c which are offset exactly or at least substantially by 180° with respect to each other in the circumferential direction, may more securely prevent rotational movements relative to the sleeve structure 4. When connected to the needle protector 7, the attaching mechanisms 9 of the needle protector 7 and the attaching mechanisms 11b of the first blocking mechanism 11 form a rotary joint with each other, with the tilting axis K as the joint axis. The attaching mechanisms 11b form the shaft of the rotary joint and the attaching mechanisms 9 form the socket of the rotary joint. The blocking mechanism 11 is shown in a position of equilibrium with respect to the axes L and K, in which it is held by the spring member 10 when installed. The tilting axis K then constantly points radially with respect to the longitudinal axis L. In said position of equilibrium, the base body 11a forms a tilting arm both to the left and to the right of the tilting axis K. One of the two tilting arms is in stopper contact with the blocking mechanism 12 in the protective position, and the other tilting arm is in stopper contact with the blocking mechanism 13 in the protective position. As shown by way of example in FIGS. 3 and 4, the attaching mechanisms 9 are divided parallel to the longitudinal axis L, such that each of the attaching mechanisms 9 forms two socket arms next to each other in the longitudinal direction L which can be elastically bent away from each other such that the first blocking mechanism 11 can be inserted via its two attaching mechanisms 11b, and the attaching mechanisms 9 elastically snap together with the attaching mechanisms 11b. For this purpose, corresponding recesses are formed in the base body 11a on both sides of the attaching mechanisms 11b, which the attaching mechanisms 9 enter when being connected and which can latch together with the attaching mechanisms 11b. The base body 11a also comprises a central passage, extending in the longitudinal direction L, for the holding region 3 of the needle base.

Figure 6:
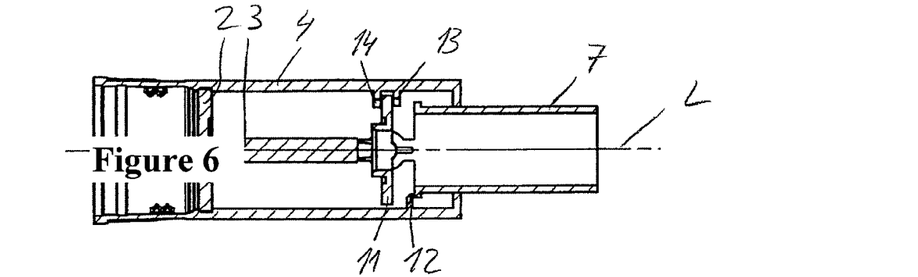
FIGS. 6-10 depict the needle protecting device in various operational positions.
Figure 7:
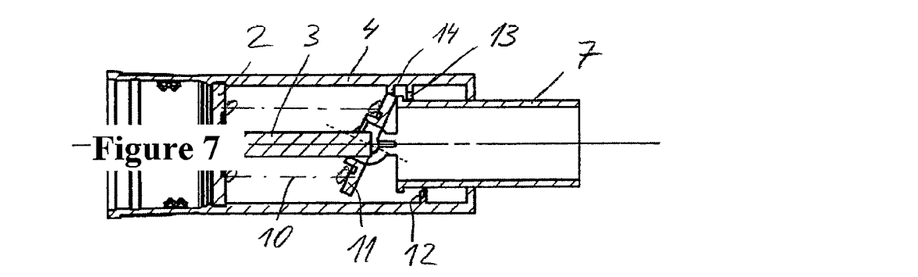
Figure 8:
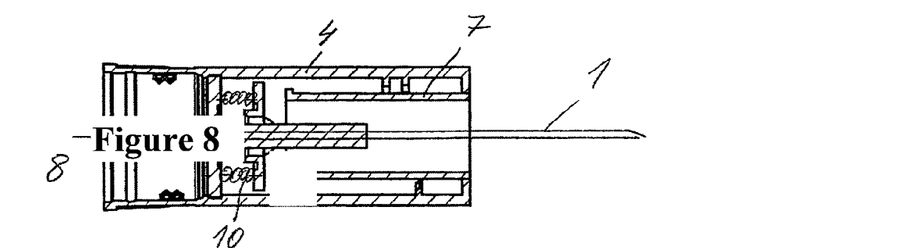

The method of operation of the needle protecting device is explained below on the basis of the sequence shown in FIGS. 6 to 10, wherein FIGS. 6 and 10 correspond to FIGS. 1 and 2.

The needle protecting device reaches the user sterilely packaged, in the initial state. The user removes the packaging parts of the sterile packaging and places the needle protecting device, in its initial state, on the distal end of the injection apparatus, such that the connecting portion of the injection needle 1 penetrates the sealing membrane of the product reservoir and the fluid connection to the hollow volume of the injection needle 1 is established.

The user places the injection apparatus, with the needle protector 7 in the initial position, onto the skin at the desired injection point and presses the injection apparatus against the skin in the distal direction, whereby the needle protector 7 experiences a force acting in the proximal direction and begins to move in the proximal (rearward) direction relative to the injection apparatus and the needle base. The spring member 10 counteracts the movement with its spring force. In the first phase of the movement, the first blocking mechanism 11—which, when the needle protector 7 is in the initial position, is still in stopper contact with the front side of the unblocking mechanism 14—tilts into the angular position shown in FIG. 7 and ultimately passes the unblocking mechanism 14. Additional pressure causes the needle protector 7 to be moved into the exposing position shown in FIG. 8, against the force of the spring member 10. In the exposing position, the needle protector 7 has completely entered the sleeve body 4. The spring force of the spring member 10 holds the first blocking mechanism 11 in its position of equilibrium, in which the left-hand and right-hand tilting arm of the blocking mechanism 11 point not only perpendicular to the tilting axis K but also at least substantially perpendicular to the longitudinal axis L. The central holding portion 3 of the needle base protrudes through the blocking mechanism 11. The injection portion of the injection needle 1 protrudes beyond the sleeve structure 4 and the needle protector 7 in the distal direction. The freely protruding length of the injection needle 1 is advantageously dimensioned such that the needle tip penetrates into the subcutaneous tissue.

Once the product has been administered, the user draws the injection needle 1 out of the tissue. Once the external force has been removed, the needle protector 7 moves back in the distal (forwardly) direction due to the force of the spring member 10.

Figure 9:
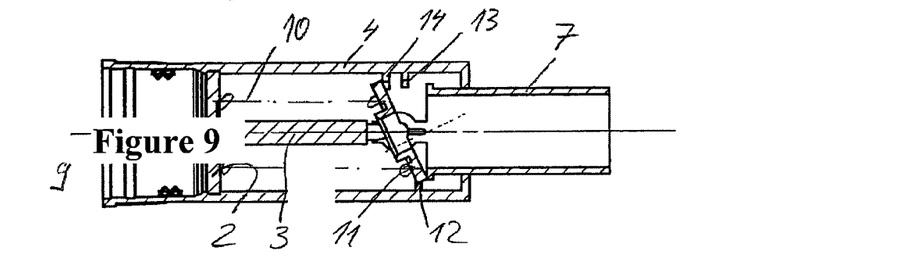

FIG. 9 shows the needle protecting device in the course of its movement in the distal direction, at the moment in which the first blocking mechanism 11 passes the blocking means. In a first phase of the movement, the first blocking mechanism 11 is completely free from the other blocking mechanisms 12 and 13 and the unblocking mechanism 14. At the end of this first phase, the blocking mechanism 11 passes into stopper contact with the unblocking mechanism 14, such that it "catches" or lodges in the stopper contact and the tilting arm on the other side of the tilting axis K, which faces the second blocking mechanism 12, tilts forwards in the distal direction. The axial distance between the stopper formed on the rear side by the unblocking mechanism 14 and the rear side of the blocking mechanism 12 is dimensioned such that the first blocking mechanism 11, in stopper contact with the unblocking mechanism 14 on the opposite side, can tilt distally in front of the blocking mechanism 12 and pass it. Once the blocking mechanism 11 has passed the blocking mechanism 12, it slips out of the stopper contact with the unblocking mechanism 14 and then also passes the third blocking mechanism 13.

Figure 10:
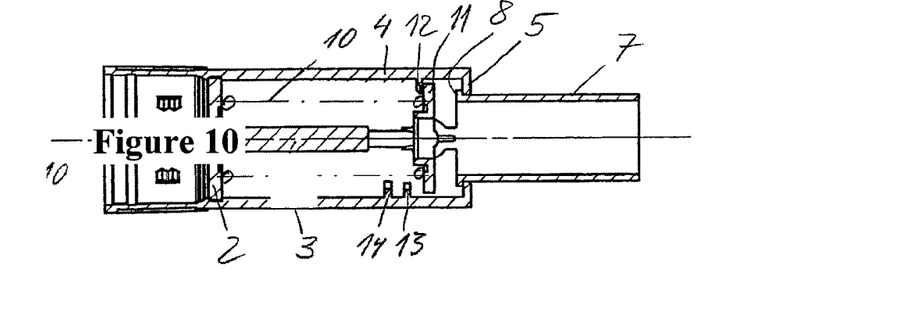

FIG. 10 shows the needle protecting device in its end state, in which the needle protector 7 assumes its distal protective position. The movement by the needle protector in the distal direction is limited by the pair of stoppers 5, 8. In the end state, the first blocking mechanism 11 assumes its position of equilibrium again and exhibits its greatest extent as measured radially with respect to the longitudinal axis L. The rear side of the first blocking mechanism 11 then faces the front sides of the blocking mechanisms 12 and 13. Pressure exerted on the needle protector 7 in the proximal direction can only cause the first blocking mechanism 11 to tilt simultaneously into stopper contact with the blocking mechanism 12 and the unblocking mechanism 14, and the needle protector 7 to thus be blocked securely in the protective position. In this state, the user can detach the needle protecting device from the injection apparatus, secure against pricking injuries, and dispose of it. Once a new needle protecting device has been attached, the injection apparatus is ready for the next injection.

The sleeve structure 4 forms a part of the locking system, not only in the form of the blocking mechanisms 12 and 13 and the unblocking mechanism 14; it is also accorded the function of protecting the blocking and unblocking mechanisms 11 to 14 from being accessed from the side. In fulfilling this protective function, the sleeve structure 4 forms a blocking portion which circumferentially envelops the entire blocking means and in which the blocking mechanisms 12 and 13 and the unblocking mechanism 14 are formed. It is also advantageous for the flange 5 which projects inwards to be formed circumferentially, as in the example embodiment, such that there is also no possibility of manipulation through the gap between the sleeve structure 4 and the needle protector 7. The user has no direct access to the blocking mechanisms 12 and 13; when the needle protector 7 is in the protective position, the user cannot even see the blocking mechanisms 12 and 13. The method of operation of the blocking means is therefore not immediately obvious, making it even more difficult to manipulate.

A needle protecting device in accordance with the present invention allows complete functional testing in the production process. When tested, the completely assembled needle protecting device is triggered, as described above for an injection, i.e. it is transferred from the initial state shown in FIG. 6 to the end state shown in FIG. 10. Testing may be performed by hand, but, in some preferred embodiments of the testing method, is performed automatically by tensing the needle protecting device by using a holding means, i.e. exerting axial pressure on the needle protector 7 in the region of the sleeve structure 4 and by a gripper or plunger, such that it moves from the initial position to the exposing position and, once the pressure is relieved, moves in the distal direction into the protective position. Once this cycle is complete, an elongated, rod-shaped tool is—likewise, possibly automatically— moved through the needle protector 7 in the longitudinal direction L up to the first blocking mechanism 11, such that it contacts the first blocking mechanism 11 on the side opposite the blocking mechanism 12. A pressure acting in the proximal direction is exerted on the blocking mechanism 11 by the tool. The pressure is sufficiently large that the spring force of the spring member 10 is overcome, and the blocking mechanism 11 tilts out of its position of equilibrium as established by the spring member 10 and can pass the blocking mechanisms 12 and 13 in the proximal direction. During this tilting movement, there is no stopper contact between the blocking mechanism 11 and blocking mechanism 12, i.e. the needle protector 7 is pressed in the distal direction by the spring member 10 via the blocking mechanism 11 until it abuts the flange 5, far enough that the first blocking mechanism 11 is free from the second blocking mechanism 12. Accordingly, "air" exists in the axial direction between the two blocking mechanisms 11 and 12. The needle protector 7 can optionally be held in stopper contact with the flange 5 by a gripping means, to prevent the blocking mechanism 11 from being able to be pressed into stopper contact with the blocking mechanism 12 by the pressure of the tool, before the first blocking mechanism 11 has passed the third blocking mechanism 13. If the blocking mechanism 11, still in contact with the tool, has passed the blocking mechanism 13 in the course of its tilting movement, the needle protector 7 is moved by applying an external force in the proximal direction, until the blocking mechanism 11 has also passed the blocking mechanism 12. As soon as this has occurred, the tool is retracted such that the blocking mechanism 11, thus relieved, can move back into its neutral position of equilibrium due to the spring force of the spring member 10, and assumes the position shown in FIG. 6, i.e. the needle protecting device is once again in the initial state.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle protecting device for an injection apparatus comprising a proximal end, a distal end, an injection needle with a needle tip and a needle base, beyond which the injection needle protrudes, said needle protecting device comprising:

a needle protector movably connected to the needle base and moveable from an initial position covering the needle tip to an exposing position in which the needle tip of the injection needle protrudes beyond the needle protector to a protective position in which it overlaps the injection needle including the needle tip;

a first blocking mechanism connected to the needle protector comprising a disc-shaped base body, two attaching mechanisms which co-operate with prongs extending from the needle protector to form a rotary joint comprising a tilting axis at a rotational axis of the rotary joint, wherein the two attaching mechanisms comprise a shaft of the rotary joint and the prongs comprise a socket of the rotary joint, two rotational blocks arranged offset with respect to each other in the circumferential direction and in a guiding engagement with axial guides of the needle protecting device, said guiding engagement preventing rotational movements of the first blocking mechanism and thus rotational movements of said needle protector about the longitudinal axis, and a central passage through which the needle base projects, wherein at equilibrium, the disc-shaped base body forms a tilting arm both to the left and right of the tilting axis; and a second blocking mechanism connected to or formed in one piece with the needle base; and wherein when the needle protector is in the protective position, the blocking mechanisms are in a blocking engagement with each other as at least one of the two tilting arms are in stopper contact with the second blocking mechanism, and said stopper contact blocks the needle protector from moving into the exposing position.

2. The needle protecting device according to claim 1, further comprising a spring member for generating a spring force which causes the needle protector to move into the protective position.

3. The needle protecting device according to claim 2, wherein the first blocking mechanism can be moved out of the blocking engagement against a restoring spring force.

4. The needle protecting device according to claim 1, wherein the first blocking mechanism is charged by a spring member with a spring force which acts in the distal direction and counteracts a movement by the first blocking mechanism relative to said one of the needle protector and the needle base.

5. The needle protecting device according to claim 4, wherein the spring member charges the needle protector via the first blocking mechanism with a spring force which causes the needle protector to move to the protective position.

6. The needle protecting device according to claim 1, further comprising a blocking portion wherein the blocking portion surrounds the needle protector or the needle protector surrounds the blocking portion, and the blocking portion or the needle protector surrounds the blocking mechanisms and protects them from being laterally accessed at least when the needle protector is in the protective position.

7. The needle protecting device according to claim 6, wherein at least one of the blocking portion or the needle protector comprises an opening through which the injection needle protrudes when the needle protector is in the exposing position, and through which a tool can be moved in the proximal direction to one of the blocking mechanisms in blocking engagement.

8. The needle protecting device according to claim 7, wherein the blocking engagement may be non-destructively released and the device restored to the initial position by the tool.

9. The needle protecting device according to claim 7, wherein the second blocking mechanism is one of formed in one piece with the blocking portion or is attached to the blocking portion such that it cannot move in the longitudinal direction of the injection needle, and forms a stopper for the first blocking mechanism which blocks the needle protector from moving into the exposing position when it assumes the protective position.

10. The needle protecting device according to claim 9, wherein the second blocking mechanism is formed by a protrusion which projects, transverse to the longitudinal length of the injection needle, from the blocking portion or the needle protector.

11. The needle protecting device according to claim 1, wherein the first blocking mechanism can be tilted relative to said one of the needle base and the needle protector and, when the needle protector is in the protective position, can be moved out of the blocking engagement by a tilting movement.

12. The needle protecting device according to claim 11, further comprising a third blocking mechanism arranged together with the second blocking mechanism such that it cannot move in the direction of the longitudinal length of the injection needle relative to the other of the needle base and the needle protector, at least when the needle protector is in the protective position, and wherein the second blocking mechanism is arranged to the left of a tilting axis of the first blocking mechanism and the third blocking mechanism is arranged to the right of the tilting axis of the first blocking mechanism and, when the needle protector is in the protective position, each form a stopper for the first blocking mechanism, and in that the stoppers are offset with respect to each other in the longitudinal direction of the length injection needle and block the needle protector from moving into the exposing position.

13. The needle protecting device according to claim 12, further comprising a blocking portion wherein the blocking portion surrounds the needle protector or the needle protector surrounds the blocking portion, and wherein the blocking portion or the needle protector surrounds the blocking mechanisms and protects them from being laterally accessed, at least when the needle protector is in the protective position, wherein the third blocking mechanism is formed by a protrusion which projects, transverse to the longitudinal length of the injection needle, from the blocking portion or the needle protector.

14. The needle protecting device according to claim 13, further comprising an unblocking mechanism which cannot be moved relative to the other of the needle base and the needle protector, at least when the needle protector is in the protective position, the unblocking mechanism arranged on the same side of the tilting axis as the third blocking mechanism and forming a stopper for the first blocking mechanism which faces away from the stoppers formed by the second blocking mechanism and third blocking mechanism in the longitudinal direction of the injection needle, and wherein the stopper formed by the unblocking mechanism is offset with respect to the stoppers formed by the second blocking mechanism and third blocking mechanism in the longitudinal direction of the injection needle.

15. The needle protecting device according to claim 14, wherein the second blocking mechanism is nearer to the stopper of the third blocking mechanism than to the stopper of the unblocking mechanism, relative to the length of the injection needle.

16. The needle protecting device according to claim 15, wherein the unblocking mechanism is formed by a protrusion which projects, transverse to the longitudinal direction of the injection needle, from the blocking portion or the needle protector.

17. The needle protecting device according to claim 1, wherein the needle protector can be moved from an initial position, in which it overlaps the injection needle including the needle tip and in which the first blocking mechanism and the second blocking mechanism are not in blocking engagement, into the exposing position.

18. The needle protecting device according to claim 1, wherein the needle protector can be moved relative to the needle base into a most distal end position which is determined by a stopper contact between the needle protector and an end stopper which is axially stationary relative to the needle base, and wherein the first blocking mechanism only passes into blocking engagement with the second blocking mechanism once the needle protector has been moved out of the end position in the direction of the exposing position.

19. The needle protecting device according to claim 1, wherein the two assigned guides of the needle protecting device are axial ribs which project inwardly on the inner surface area of said needle protecting device wherein the rotational blocks may be replaced with recesses.

* * * * *